United States Patent [19]

Mason et al.

[11] Patent Number: 5,672,152
[45] Date of Patent: Sep. 30, 1997

[54] HINGE FOR AN ORTHOPEDIC BRACE HAVING AN ADJUSTABLE RANGE OF ROTATION

[75] Inventors: Bradley R. Mason, Olivenhain; Jeffrey T. Mason, Escondido, both of Calif.

[73] Assignee: Breg, Inc., Vista, Calif.

[21] Appl. No.: 563,659

[22] Filed: Nov. 28, 1995

[51] Int. Cl.$^6$ .................................................. A61F 5/01
[52] U.S. Cl. .................................... 602/26; 602/16
[58] Field of Search .................................. 602/5, 16, 23, 602/26, 20

[56] References Cited

U.S. PATENT DOCUMENTS

| | | |
|---|---|---|
| 401,933 | 4/1889 | De Camp . |
| 3,439,672 | 4/1969 | Fisher .................................. 602/16 |
| 4,481,941 | 11/1984 | Rolfes . |
| 4,620,532 | 11/1986 | Houswerth .......................... 602/16 |
| 4,817,588 | 4/1989 | Bledsoe .............................. 602/16 |
| 4,982,732 | 1/1991 | Morris ................................ 602/16 |
| 5,000,169 | 3/1991 | Swicegood et al. . |
| 5,062,858 | 11/1991 | Broeck et al. .................. 602/16 X |
| 5,292,303 | 3/1994 | Bastyr et al. . |
| 5,409,449 | 4/1995 | Nebolon ............................. 602/16 |
| 5,443,444 | 8/1995 | Pruyssers ........................ 602/5 X |
| 5,460,599 | 10/1995 | Davis et al. .................... 602/16 X |

*Primary Examiner*—Richard J. Apley
*Assistant Examiner*—David R. Risley
*Attorney, Agent, or Firm*—Rodney F. Brown

[57] ABSTRACT

A hinge is provided for an orthopedic brace having an adjustable range of rotation. The hinge includes an outer member and an inner member that are rotatably connected in parallel alignment to one another. The peripheral edge of the outer member has a plurality of rotation limiting notches formed therein and the peripheral edge of the inner member has a rotation limiting face formed therein that is selectively alignable with one of the rotation limiting notches. Each of the peripheral edges also has a locking notch formed therein that is selectively alignable with the other. A rotation limiting stop is provided at the peripheral edge of the inner and outer members that is selectively positionable in one of the rotation limiting notches to define an adjustable range of rotation during a rotational mode of hinge operation. Rotation of the inner member is limited when the rotation limiting face engages the rotation limiting stop positioned in the selected notch. Alternatively, the rotation limiting stop is selectively positionable in the locking notches to lock the hinge against rotation in a locked mode of hinge operation. The hinge also includes a biasing assembly that biases the rotation limiting stop in a radially inward direction perpendicular to the axis of hinge rotation, thereby retaining the stop in a selected position against the peripheral edge of the outer member during the rotational or locked mode of hinge operation. The biasing assembly, however, enables elastic radial displacement of the rotation limiting stop in a radially outward direction when a radially outward displacement force is externally applied to the stop. The rotation limiting stop returns to a position against the peripheral edge of the outer member when the displacement force is withdrawn.

22 Claims, 5 Drawing Sheets

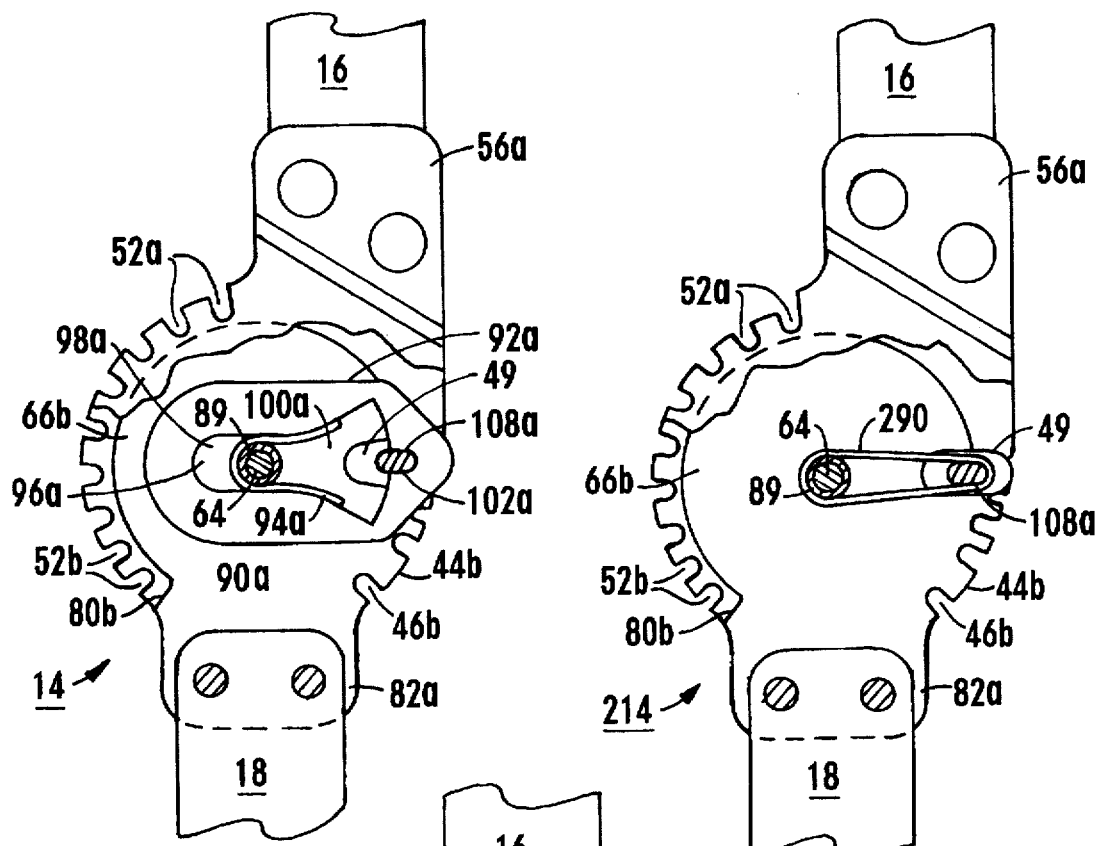
Fig. 3
Fig. 4
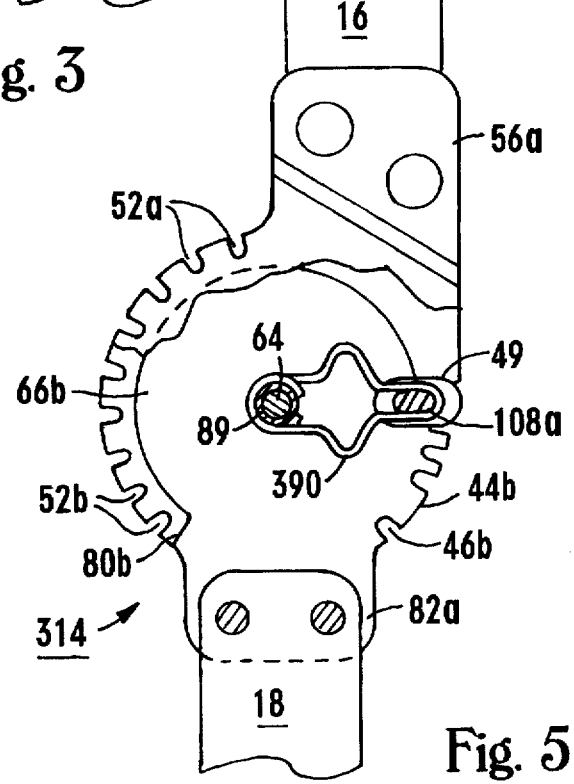
Fig. 5

HINGE FOR AN ORTHOPEDIC BRACE HAVING AN ADJUSTABLE RANGE OF ROTATION

TECHNICAL FIELD

The present invention relates generally to orthopedic braces, and more particularly to a hinge for an orthopedic brace, wherein the hinge has a range of rotation that is adjustable by means of a stop selectively positionable in one of a plurality of notches formed in the periphery of the hinge.

BACKGROUND OF THE INVENTION

Hinges for orthopedic braces having an adjustable range of rotation in the extension and flexion direction are well known in the art, for example, as disclosed by U.S Pat. No. 4,481,941 to Rolfes. The hinge of Rolfes is provided with a pair of threaded screws that function as stops to limit rotation of the hinge. Each screw is selectively threadably securable in one of a plurality of correspondingly threaded holes formed in the body of the hinge. The range of rotation of the hinge is a function of the specific holes selected by the user. Thus, each hole provides the hinge with a different range of rotation when a screw is threadably secured therein. The range of rotation of the hinge is adjusted by unscrewing at least one of the screws from its respective hole and rescrewing the screw into another hole. It has been found, however, that the task of adjusting the range of rotation of the hinge can be difficult because sufficient dexterity is required to maneuver the relatively small screws into and out of the threaded holes and because the screws are susceptible to being misplaced or lost during this task.

An alternate adjustable hinge disclosed by U.S. Pat. No. 401,933 to De Camp, facilitates adjusting the rotational range of the hinge by substituting pins for threaded screws to limit rotation of the hinge. The pins have a smooth surface that enables them to slide into and out of the holes formed in the body of the hinge. The pins are secured in the selected holes of the hinge by means of a leaf spring attached to each pin that biases the pin into its respective hole in a direction parallel to the axis of hinge rotation. Repositioning the pins of De Camp requires less dexterity than repositioning the screws of Rolfes. Nevertheless, adjusting the rotational range of the hinge of De Camp is not entirely without difficulty because a degree of dexterity is still required to pry the leaf spring away from the body of the hinge and remove the pin from the hole. As such, a hinge for an orthopedic brace having an adjustable range of rotation is needed, wherein the hinge is relatively easy to adjust to a desired rotational range in the extension or flexion direction.

Accordingly, it is an object of the present invention to provide a hinge for an orthopedic brace having an adjustable range of rotation in the extension and flexion directions. It is another object of the present invention to provide such a hinge for an orthopedic brace, wherein the hinge has a stop that readily enables adjustment of the rotational range of the hinge by selectively positioning the stop in one of a plurality of rotation limiting positions around the periphery of the hinge. It is still another object of the present invention to provide such a hinge for an orthopedic brace, wherein the stop is resistant to inadvertent slippage from its selected rotation limiting position during rotation of the hinge, yet the stop is readily repositionable to an alternately selected rotation limiting position during adjustment of the rotational range of the hinge. It is a further object of the present invention to provide a hinge for an orthopedic brace, wherein the hinge is lockable to prevent rotation thereof. It is still a further object of the present invention to provide such a hinge for an orthopedic brace, wherein the hinge has a stop that readily enables locking the hinge against rotation by selectively positioning the stop in a locked position at the periphery of the hinge. These objects and others are achieved by the invention described hereafter.

SUMMARY OF THE INVENTION

The present invention is a hinge for an orthopedic brace comprising an outer member and an inner member that are parallelly aligned and rotatably connected by a concentric pivotal connector. The peripheral edge of the outer member has a plurality of rotation limiting notches formed therein and the peripheral edge of the inner member has a rotation limiting face formed therein that is selectively alignable with one of the rotation limiting notches in the outer member by rotation of the inner member relative to the outer member about the pivotal connector. Each of the peripheral edges also has a locking notch formed therein that is selectively alignable with the other by rotation of the outer or inner member about the pivotal connector. A rotation limiting stop is provided at the peripheral edge of the inner and outer members that is rotatable relative to the outer member about the pivotal connector. The rotation limiting stop is selectively positionable in one of the rotation limiting notches in the outer member to define an adjustable range of rotation of the inner member about the pivotal connector during a rotational mode of hinge operation. Rotation of the inner member is limited when the rotation limiting face of the inner member engages the rotation limiting stop positioned in a selected notch during rotation of the inner member relative to the outer member. Alternatively, the rotation limiting stop is selectively positionable in the locking notches of the outer and inner members to lock the outer and inner members against rotation about the pivotal connector during a locked mode of hinge operation.

The hinge additionally comprises a biasing assembly that biases the rotation limiting stop in a radially inward direction perpendicular to the axis of rotation of the outer member, thereby retaining the rotation limiting stop in a selected position against the peripheral edge of the outer member during the rotational or locked mode of hinge operation, when no counterforce is externally applied to the rotation limiting stop. The biasing assembly has an elastic element that is rotatably anchored to one of the hinge components enabling radial displacement of the rotation limiting stop in a radially outward direction when a radially outward displacement force is externally applied to the rotation limiting stop countering the radially inward biasing force during an adjustment mode of hinge operation. The elastic element also enables return of the rotation limiting stop to a position against the peripheral edge of the outer member when the displacement force is withdrawn upon completion of the adjustment mode of hinge operation and resumption of the rotational or locked mode of hinge operation.

In a preferred embodiment, the hinge is augmented with a second rotation limiting stop and an associated second biasing assembly that is substantially identical to the above-described first rotation limiting stop and associated first biasing assembly. In this embodiment, one rotation limiting stop is positionable on the forward arc of the peripheral edge of the outer and inner members to reside in one of the rotation limiting notches formed therein and serve as a rotation limiting stop for a first direction of rotation. The other rotation limiting stop is opposingly positionable on the rearward arc of the peripheral edge of the outer and inner members to reside in one of the rotation limiting notches formed therein and serve as a rotation limiting stop for the opposite direction of rotation. In the preferred embodiment, the hinge is further provided with a redundant second set of outer and inner members that is substantially identical to the first set described above. The second set is parallelly and concentrically alignable with the first set to operate in a complimentary manner therewith.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 3 is a partial cutaway frontal view of the hinge of FIG. 1.

FIG. 4 is a partial cutaway frontal view of an alternate embodiment of the hinge of the present invention.

FIG. 5 is a partial cutaway frontal view of another alternate embodiment of the hinge of the present invention.

DESCRIPTION OF PREFERRED EMBODIMENTS

Figure 1:
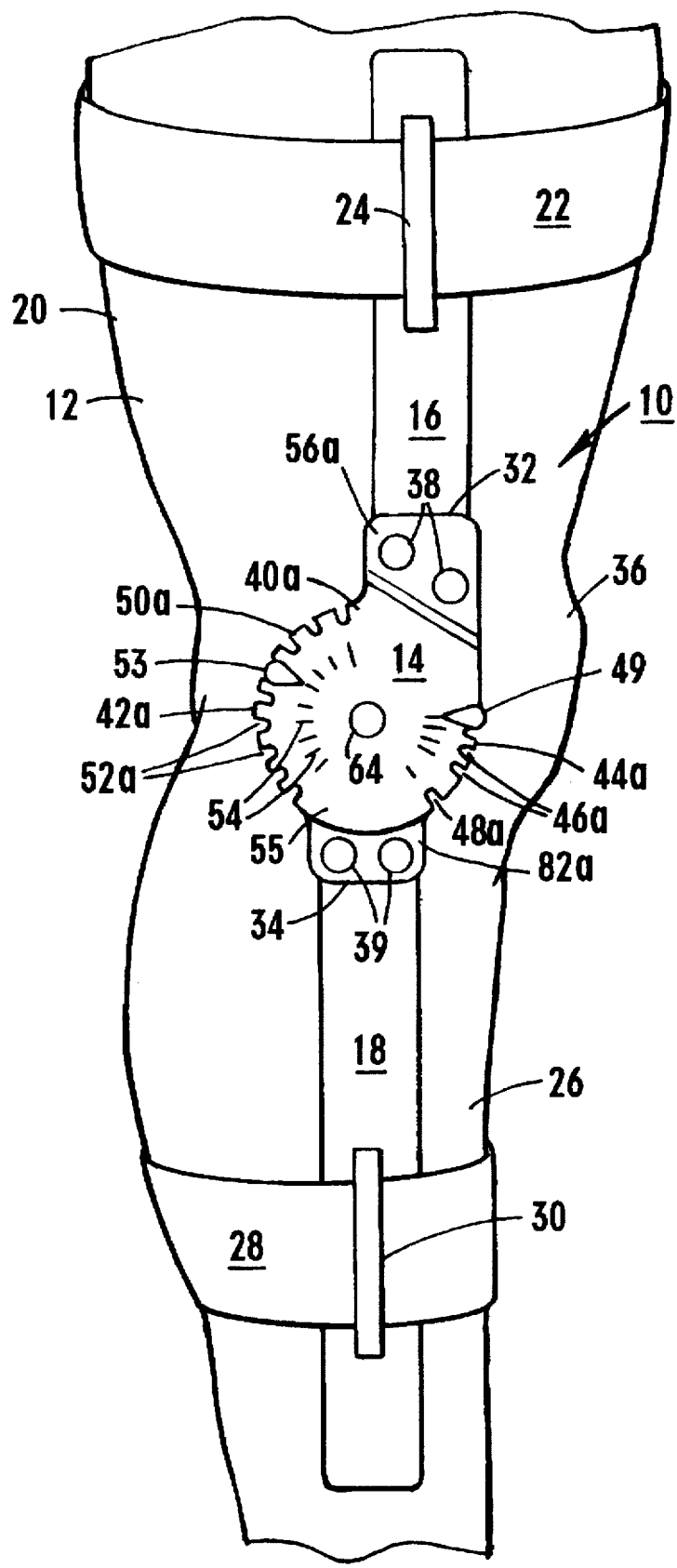
FIG. 1 is a side view of a leg having an orthopedic brace employing the hinge of the present invention mounted thereon.

Referring initially to FIG. 1, a hinged orthopedic brace is shown and generally designated 10. For purposes of illustration, the hinged orthopedic brace 10 shown and described herein is a postoperative knee brace mounted on the right leg 12 of a user, although it is understood that the skilled artisan can readily adapt the instant postoperative knee brace 10 to the opposite leg or to other types of hinged braces for the knee or other joints of the body in accordance with the instant teaching. The brace 10 comprises a novel hinge 14 in combination with conventional components including an upper arm 16 and a lower arm 18. Both the upper and lower arms 16, 18 are substantially rigid, preferably formed from a lightweight, high-strength material such as aluminum or stainless steel. The upper arm 16 extends substantially the length of the upper leg 20 and is retained in removable engagement therewith by means of an adjustable upper leg strap 22 threaded through an upper strap loop 24 on the upper arm 16. The lower arm 18 extends substantially the length of the lower leg 26 and is similarly retained in removable engagement therewith by means of an adjustable lower leg strap 28 threaded through a lower strap loop 30 on the lower arm 18. Although not shown, additional upper and lower leg straps and strap loops can be provided to further secure the brace 10 to the leg 12. The upper and lower arms 16, 18 have upper and lower proximal ends 32, 34, respectively, that are oriented proximal to the knee joint 36 and are attached to the hinge 14 by conventional fasteners 38, 39, such as fastening rivets shown here.

The hinge 14 is configured to provide the brace 10 with an adjustable range of extension and flexion rotation during a rotational mode of hinge operation. Alternatively, the hinge 14 is configured to enable locking the brace 10 against rotation during a locked mode of hinge operation. The terms "anterior" and "posterior" are used hereafter to identify various hinge components. The terms describe the orientation of a given component relative to the hinge 14, rather than relative to the knee joint 36.

The hinge 14 comprises an anterior outer member 40a adapted to be positioned on the front side of the hinge 14 distal to the knee joint 36. The anterior outer member 40a is formed from a rigid, lightweight, high-strength material, such as aluminum or stainless steel, and has a planar, substantially circular configuration bordered by a peripheral edge 42a defining the circumference of the anterior outer member 40a. The forward arc 44a of the peripheral edge 42a has a plurality of extension limiting notches 46a and a locking notch 48a formed therein that are disposed at circumferentially spaced intervals along the forward arc 44a to receive an extension limiting stop 49 selectively positioned adjacent to the forward arc 44a. The rearward arc 50a of the peripheral edge 42a has a plurality of flexion limiting notches 52a formed therein that are disposed at circumferentially spaced intervals along the rearward arc 50a to receive a flexion limiting stop 53 selectively positioned adjacent to the rearward arc 50a. The notches 46a, 48a, 52a shown herein are U-shaped, but it is understood that substantially any open-ended indentation in the peripheral edge 42a can function as notches 46a, 48a, 52a. A plurality of rotation limit markers 54 are provided on the face 55 of the anterior outer member 40a. The markers 54 are positioned radially inward from the peripheral edge 42a and each marker 54 is aligned with a corresponding extension limiting notch 46a, locking notch 48a, or flexion limiting notch 52a, respectively. The anterior outer member 40a is provided with a fastening extension 56a enabling attachment of the anterior outer member 40a to the proximal end 32 of the upper arm 16 of the brace 10. Although the anterior outer member 40a and upper arm 16 are described herein as distinctly separate structures fastened together by the fasteners 38, it is apparent that the upper arm 16 and anterior outer member 40a can also be integrally formed as a single unitary structure within the scope of the present invention obviating the presence of the fasteners 38.

Figure 2A:
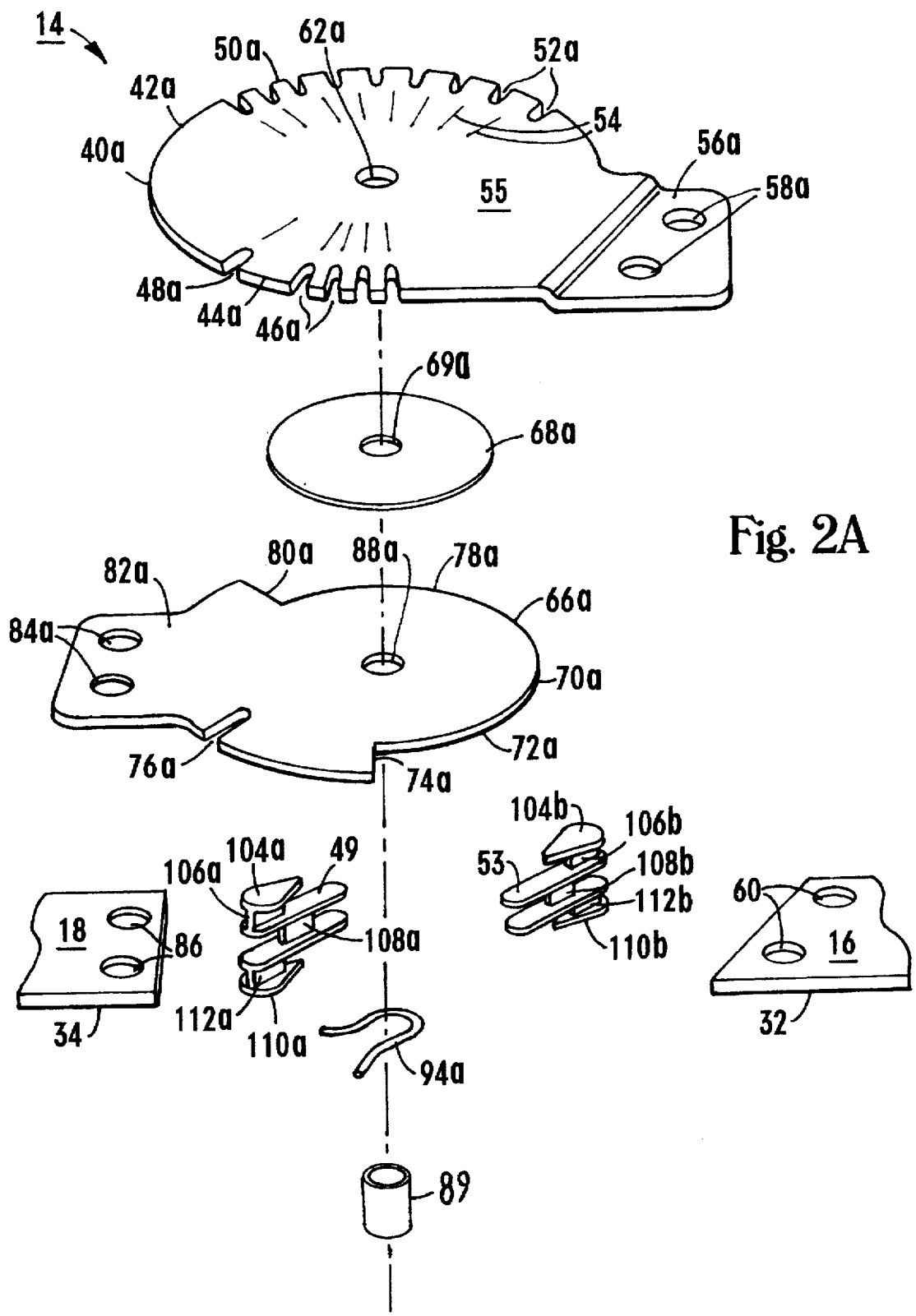
FIGS. 2A and 2B in combination are an exploded perspective view of the hinge of FIG. 1.
Figure 2B:
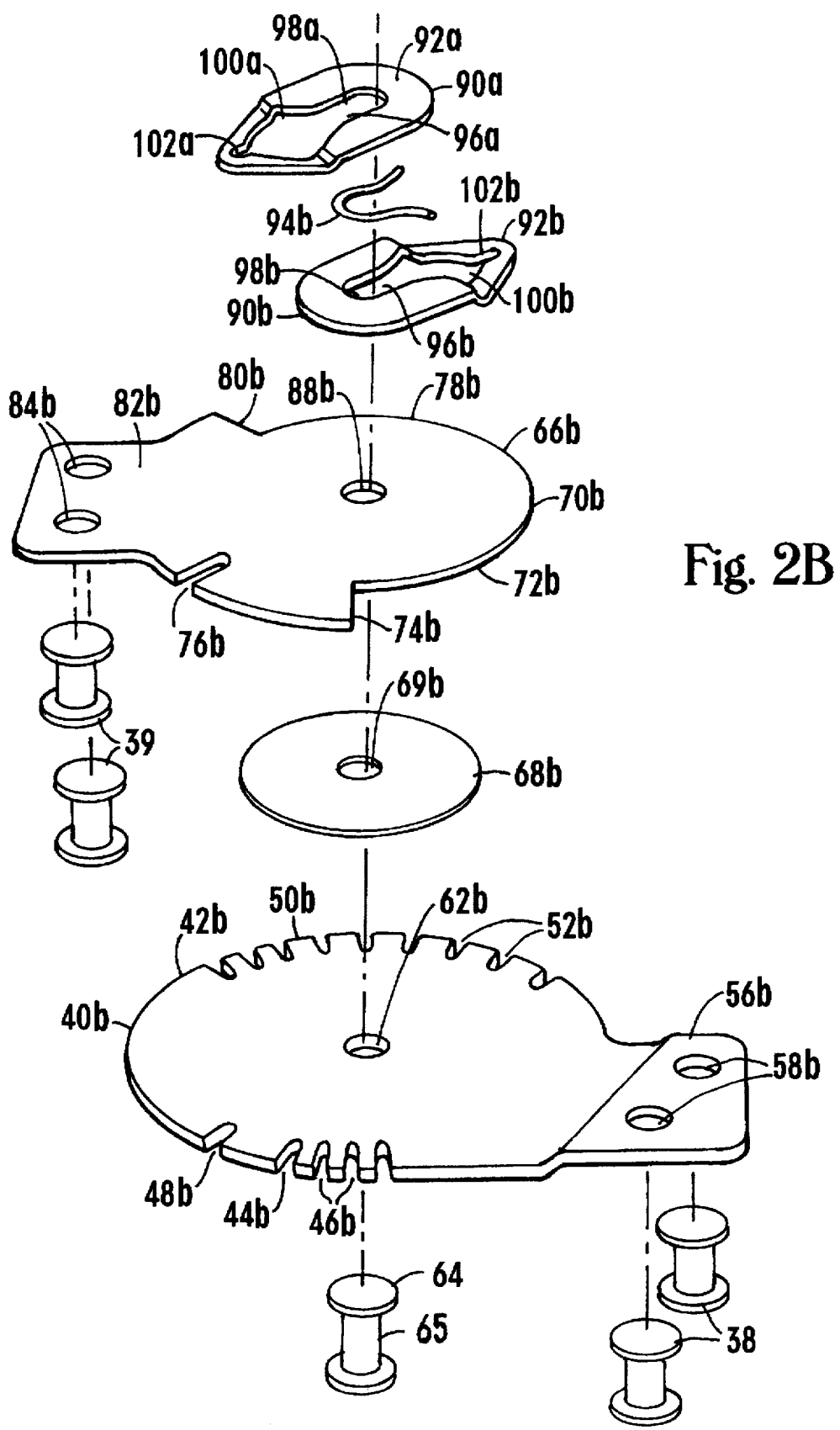

Referring additionally to FIGS. 2A and 2B in association with FIG. 1, the fastening extension 56a is shown to have a pair of fastening apertures 58a formed therethrough to receive the fasteners 38. The proximal end 32 of the upper arm 16 likewise has a pair of fastening apertures 60 correspondingly formed therethrough to receive the fasteners 38. The anterior outer member 40a is provided with a pivot aperture 62a formed through the center thereof to receive a pivotal connector comprising a pivoting rivet 64, wherein the body 65 of the pivoting rivet 64 has an outside diameter substantially equal to the diameter of the pivot aperture 62a.

The hinge 14 further comprises a posterior outer member 40b that is substantially identical to the anterior outer member 40a, but is adapted to be positioned on the back side of the hinge 14 proximal to the knee joint 36. Components of the posterior outer member 40b corresponding to like components of the anterior outer member 40a are identified by the same reference number as the components of the anterior outer member 40a, but are distinguished by the suffix "b." Accordingly, the posterior outer member 40b has a peripheral edge 42b with a forward arc 44b, including a plurality of extension limiting notches 46b and a locking notch 48b to receive the extension limiting stop 49, and a rearward arc 50b including a plurality of flexion limiting notches 52b to receive the flexion limiting stop 53. The anterior and posterior outer members 40a, 40b are concentrically positioned in parallel planes on opposite sides of the hinge 14 and are rotationally fixed relative to each other such that the notches 46a, 48a, 52a in the peripheral edge 42a of the anterior outer member 40a are fixably aligned with their counterpart notches 46b, 48b, 52b in the peripheral edge 42b of the posterior outer member 40b. The posterior outer member 40b is provided with a fastening extension 56b and fastening apertures 58b enabling attachment of the posterior outer member 40b to the proximal end 32 of the upper arm 16 of the brace 10 in a like manner as the anterior outer member 40a. In the alternative, it is noted that the upper arm 16 and posterior outer member 40b can likewise be integrally formed as a single unitary structure within the scope of the present invention. The posterior outer member 40b is also provided with a pivot aperture 62b formed through the center thereof in alignment with the pivot aperture 62a of the anterior outer member 40a to similarly receive the pivoting rivet 64.

The hinge 14 further has an anterior inner member 66a and a posterior inner member 66b concentrically positioned between the anterior and posterior outer members 40a, 40b. The anterior inner member 66a is separated from the anterior outer member 40a by an anterior washer 68a and the posterior inner member 66b is similarly separated from the posterior outer member 40b by a posterior washer 68b. The anterior and posterior washers 68a, 68b are substantially identical circular disks, each having a pivot aperture 69a, 69b, respectively, in concentric alignment with each other and with the pivot apertures 62a, 62b of the anterior and posterior outer members 40a, 40b, respectively. The anterior and posterior inner members 66a, 66b are aligned in parallel planes relative to each other and relative to the anterior and posterior outer members 40a, 40b. The anterior and posterior inner members 66a, 66b are also rotationally fixed relative to each other, but are rotatable in unison relative to the anterior and posterior outer members 40a, 40b, during the rotational mode of hinge operation.

Like the anterior and posterior outer members 40a, 40b, the anterior inner member 66a is formed from a rigid, lightweight, high-strength material, such as aluminum or stainless steel, and has a planar, substantially circular configuration bordered by a peripheral edge 70a defining the circumference of the anterior inner member 66a . The forward arc 72a of the peripheral edge 70a has an extension limiting face 74a and a locking notch 76a formed therein that are disposed at a circumferentially spaced interval along the forward arc 72a. The extension limiting face 74a is provided to abut the extension limiting stop 49 and the locking notch 76a is provided to receive the extension limiting stop 49, respectively. The rearward arc 78a of the peripheral edge 70a has a flexion limiting face 80a formed therein to abut the flexion limiting stop 53. The anterior inner member 66a is provided with a fastening extension 82a enabling attachment of the anterior inner member 66a to the proximal end 34 of the lower arm 18 of the brace 10. The fastening extension 82a has a pair of fastening apertures 84a formed therethrough to receive the fasteners 39. The proximal end 34 of the lower arm 18 likewise has a pair of fastening apertures 86 correspondingly formed therethrough to receive the fasteners 39. It is noted that although the anterior inner member 66a and lower arm 18 are described herein as distinctly separate structures fastened together by the fasteners 38, it is apparent that the upper arm 16 and anterior inner member 66a can also be integrally formed as a single unitary structure within the scope of the present invention obviating the presence of the fasteners 39. The anterior inner member 66a is further provided with a pivot aperture 88a formed through the center thereof in alignment with the pivot apertures 62a, 62b, 69a, 69b of the anterior and posterior outer members 40a, 40b and the anterior and posterior washers 68a, 68b, respectively.

The posterior inner member 66b is substantially identical to the anterior inner member 66a, but the anterior inner member 66a is adapted to be positioned proximal to the anterior outer member 40a, while the posterior inner member 66b is adapted to be positioned proximal to the posterior outer member 40b. Components of the posterior inner member 66b corresponding to like components of the anterior inner member 66a are identified by the same reference number as the components of the anterior inner member 66a, but are distinguished by the suffix "b." Accordingly, the posterior inner member 66b has a peripheral edge 70b with a forward arc 72b, including an extension limiting face 74b to abut the extension limiting stop 49 and a locking notch 76b to receive the extension limiting stop 49, and a rearward arc 78b, including a flexion limiting face 80b to abut the flexion limiting stop 53. The anterior and posterior inner members 66a, 66b are opposingly positioned such that the rotation limiting faces 74a, 80a in the peripheral edge 70a of the anterior inner member 66a are fixably aligned with their counterpart rotation limiting faces 74b, 80b in the peripheral edge 70b of the posterior inner member 66b . The locking notch 76a in the peripheral edge 70a of the anterior inner member 66a is also fixably aligned with its counterpart locking notch 76b in the peripheral edge 70b of the posterior inner member 66b. The posterior inner member 66b is provided with a fastening extension 82b and fastening apertures 84b enabling attachment of the posterior inner member 66b to the proximal end 34 of the lower arm 18 of the brace 10 in a like manner as the anterior inner member 66a. In the alternative, it is noted that the lower arm 18 and posterior inner member 66b can be integrally formed as a single unitary structure within the scope of the present invention. The posterior inner member 66b is also provided with a pivot aperture 88b formed through the center thereof in alignment with the pivot apertures 62a, 62b, 69a, 69b, 88a of the anterior and posterior outer members 40a, 40b, the anterior and posterior washers 68a, 68b, and the anterior inner member 66a, respectively. Each of the pivot apertures 69a, 69b, 88a, 88b of the anterior and posterior washers 68a, 68b and the anterior and posterior inner members 66a, 66b, respectively, has a substantially equal diameter that is greater than the diameter of the pivot apertures 62a , 62b of the anterior and posterior outer members 40a, 40b.

In addition to the pivoting rivet 64, the pivotal connector comprises a cylindrical bushing 89 rotatably retained around the body 65 of the pivoting rivet 64. The bushing 89 has an inside diameter substantially equal to the outside diameter of the body 65 and has an outside diameter substantially equal to the diameter of the pivot apertures 69a, 69b, 88a, 88b. Accordingly, the bushing 89 is received by the pivot apertures 69a, 69b, 88a, 88b, but not by the pivot apertures 62a, 62b, thereby enabling the anterior and posterior inner members 66a, 66b to rotate in unison about the pivotal connector 64, 89 relative to the anterior and posterior outer members 40a, 40b.

The hinge 14 additionally has an anterior biasing assembly 90a and a posterior biasing assembly 90b concentrically positioned between the anterior and posterior inner members 66a, 66b. The anterior and posterior biasing assemblies 90a, 90b are aligned in substantially parallel planes relative to each other and relative to the outer and inner members 40a, 40b, 66a, 66b and washers 68a, 68b. The anterior and posterior biasing assemblies 90a, 90b are rotationally fixed relative to the anterior and posterior outer members 40a, 40b, during the rotational and locked modes of hinge operation, but are rotatable relative to the anterior and posterior outer members 40a, 40b, during the adjustment mode of hinge operation.

The anterior biasing assembly 90a comprises a slidable member 92a and a spring 94a retained within the slidable member 92a. The slidable member 92a is formed from a rigid or a flexible material that is substantially nonstretchable, such as a suitable metal or plastic. The slidable member 92a has a substantially flat elongate configuration that is tapered in a radial direction extending away from the pivotal connector 64, 89. A longitudinal slot 96a is provided along the longitudinal axis of the slidable member 92a. The longitudinal slot 96a is characterized by three segments, an anchor segment 98a, a spring segment 100a, and a stop segment 102a. The anchor segment 98a is at one end of the longitudinal slot 96a and is aligned with the pivot apertures 62a, 62b, 69a, 69b, 80a, 80b of the anterior and posterior outer members 40a, 40b, the anterior and posterior washers 68a, 68b, and the anterior and posterior inner members 66a, 66b, respectively, to engage the pivotal connector 64, 89. With additional reference to FIG. 3, wherein the anterior inner member 66a, the anterior washer 68a, the posterior biasing assembly 90b and the flexion limiting stop 53 are omitted for clarity, the anchor segment 98a of the anterior biasing assembly 90a is shown to be symmetrically configured, having a width substantially equal to the outside diameter of the bushing 89, but having a length substantially greater than the outside diameter of the bushing 89. This configuration enables slidable displacement of the slidable member 92a in a radial direction past the pivotal connector 64, 89 along the longitudinal axis of the anchor segment 98a during the adjustment mode of hinge operation.

The spring segment 100a is a widened portion near the midpoint of the longitudinal slot 96a that conforms to the configuration of the spring 94a. The spring 94a is an elastically-deformable curved band having flared ends that are seated against the sides of the conformed spring segment 100a and having a closed end opposite the flared ends that extends into the anchor segment 98a. The closed end of the spring 94a curves around the pivotal connector 64, 89 as it passes through the anchor segment 98a, thereby anchoring the slidable member 92a and spring 94a. The stop segment 102a is positioned at the opposite end of the longitudinal slot 96a from the anchor segment 98a and is a tapering of the slot 96a to engage and retain the extension limiting stop 49 therein.

The posterior biasing assembly 90b is substantially identical to the anterior biasing assembly 90a, but the anterior biasing assembly 90a is adapted to be positioned proximal to the anterior inner member 66a, while the posterior biasing assembly 90b is adapted to be positioned proximal to the posterior inner member 66b. Components of the posterior biasing assembly 90b corresponding to like components of the anterior biasing assembly 90a are identified by the same reference number as the components of the anterior biasing assembly 90b, but are distinguished by the suffix "b." Accordingly, the posterior biasing assembly 90b comprises a slidable member 92b and a spring 94b retained therein. The slidable member 92b has a longitudinal slot 96b characterized by an anchor segment 98b, a spring segment 100b, and a stop segment 102b. The anchor segment 98b is aligned with the anchor segment 98a of the slidable member 92a and with the pivot apertures 62a, 62b, 69a, 69b, 80a, 80b of the anterior and posterior outer members 40a, 40b, the anterior and posterior washers 68a, 68b, and the anterior and posterior inner members 66a, 66b, respectively, to engage the pivotal connector 64, 89. The slidable member 92b is slidably displacable in a radial direction past the stationary pivotal connector 64, 89 along the longitudinal axis of the anchor segment 98b during the adjustment mode of hinge operation. The spring segment 100b conforms to the configuration of the spring 94b. The spring has flared ends seated against the sides of the spring segment 100b and has a closed end that extends into the anchor segment 98b around the pivotal connector 64, 89 to anchor the slidable member 92b and spring 94b. The stop segment 102b is tapered to engage and retain the flexion limiting stop 53 therein.

The extension limiting stop 49 of the hinge 14 is positioned in abutment with the forward arcs 44a, 44b of the peripheral edges 42a, 42b of the anterior and posterior outer members 40a, 40b, respectively. The extension limiting stop 49 comprises an anterior head 104a, an anterior post 106a, a midpost 108a, a posterior head 110a and a posterior post 112a. The anterior post 106a is configured to conformingly fit within the extension limiting notches 46a and locking notches 48a, 76a and to fit in abutment with the extension limiting face 74a. The anterior head 104a sits atop the anterior post 106a and is configured to facilitate retention of the anterior post 106a in the notches 46a, 48a, 76a. The anterior head 104a is tapered in the radial direction of the pivotal connector 64, 89, thereby forming a pointer that points to the rotation limit marker 54 on the face 55 of the anterior outer member 40a aligned with the notch 46a or 48a in which the anterior post 104a is retained. The posterior post 112a is similarly configured to conformingly fit within the extension limiting notches 46b and locking notches 48b, 76b and to fit in abutment with the extension limiting face 74b. The posterior head 110a sits atop the posterior post 112a and is configured to facilitate retention of the posterior post 112a in the notches 46b and 48b. The midpost 108a is in a recessed position between the anterior and posterior posts 106a, 112a and is configured to be received by the stop segment 102a of the longitudinal slot 96a. The slidable member 92a extends around the midpost 108a and, in cooperation with the spring 94a, elastically biases the extension limiting stop 49 radially inward in a direction substantially perpendicular to the axis of rotation of the hinge 14 toward the pivotal connector 64, 89 and away from the forward arcs 44a, 44b of the peripheral edges 42a, 42b.

The flexion limiting stop 53 of the hinge 14 is similarly positioned in abutment with the rearward arcs 50a, 50b of the peripheral edges 42a, 42b of the anterior and posterior outer members 40a, 40b, respectively. The flexion limiting stop 53 is substantially identical to the extension limiting stop 49. Components of the flexion limiting stop 53 corresponding to like components of the extension limiting stop 49 are identified by the same reference number as the components of the extension limiting stop 49, but are distinguished by the suffix "b." Accordingly, the flexion limiting stop 53 comprises an anterior head 104b, an anterior post 106b, a midpost 108b, a posterior head 110b and a posterior post 112b. The anterior post 106b conformingly fits within the flexion limiting notches 52a and fits in abutment with the flexion limiting face 80a. The anterior head 104b sits atop the anterior post 106b and facilitates retention of the anterior post 106b in the notches 52a. The posterior post 112b similarly conformingly fits within the flexion limiting notches 52b and fits in abutment with the flexion limiting face 80b. The posterior head 110b sits atop the posterior post 112b and facilitates retention of the posterior post 112b in the notches 52b. The midpost 108b is in a recessed position between the anterior and posterior posts 106b, 112b and is received by the stop segment 102b of the longitudinal slot 96b. The slidable member 92b extends around the midpost 108b and, in cooperation with the spring 94b, elastically biases the flexion limiting stop 53 radially inward in a direction substantially perpendicular to the axis of rotation of the hinge 14 toward the pivotal connector 64, 89 and away from the rearward arcs 50a, 50b of the peripheral edges 42a, 42b. The hinge 14 has been described above with the outer anterior and posterior members 40a, 40b connected to the upper arm 16 and with the inner anterior and posterior members 66a, 66b connected to the lower arm 18. It is apparent to the skilled artisan that the hinge 14 can be modified within the scope of the present invention to reverse this configuration, connecting the inner anterior and posterior members 66a, 66b to the upper arm 16 and the outer anterior and posterior members 40a, 40b to the lower arm 18. The hinge 14 can correspondingly be modified by reversing the locations of the extension and flexion limiting stops 49, 53 and notches 46a, 46b, 52a, 52b, locating the extension limiting stop 49 and notches 46a, 46b in the rearward arc 50a of the peripheral edge 42a and locating the flexion limiting stop 53 and notches 52a, 52b in the forward arc 44a of the peripheral edge 42a.

Referring to FIG. 4, an alternate embodiment of a hinge of the present invention is shown and generally designated 214. The hinge 214 is substantially identical to the hinge 14 except that the biasing assemblies 90a, 90b of the hinge 14 are replaced with a pair of alternate means for biasing the extension and flexion limiting stops 49, 53 in the direction perpendicular to the axis of rotation of the hinge 214. For purposes of clarity, only one biasing assembly of the hinge 214 is shown, i.e., the anterior biasing assembly 290. It is understood that the posterior biasing assembly of the hinge 214 is substantially the same as the anterior biasing assembly 290. It is further noted that the remainder of the hinge 214 is only shown in part insofar as the remaining components of the hinge 214 are identical to those of the hinge 14. The anterior biasing assembly 290 of the hinge 214 consists of an elastic band forming an elongated closed loop. The band 290 is formed from an elastic, stretchable material such as an elastomeric material. The band 290 extends around the midpost 108a of the extension limiting stop 49 and around the pivotal connector 64, 89 to bias the extension limiting stop 49 radially inward in a direction substantially perpendicular to the axis of rotation of the hinge 214 toward the pivotal connector 64, 89 and away from the forward arcs 44a, 44b of the peripheral edges 42a, 42b.

Referring to FIG. 5, another alternate embodiment of a hinge of the present invention is shown and generally designated 314. The hinge 314 is substantially identical to the hinge 14 except that the biasing assemblies 90a, 90b of the hinge 14 are replaced with a pair of alternate means for biasing the extension and flexion limiting stops 49, 53 in the direction perpendicular to the axis of rotation of the hinge 314. For purposes of clarity, only one biasing assembly of the hinge 314 is shown, i.e., the anterior biasing assembly 390. It is understood that the posterior biasing assembly of the hinge 314 is substantially the same as the anterior biasing assembly 390. It is further noted that the remainder of the hinge 314 is only shown in part insofar as the remaining components of the hinge 314 are identical to those of the hinge 14. The anterior biasing assembly 390 of the hinge 314 consists of a length of wire bent in the shape of an elongated closed loop having a widened midsection. The assembly 390 extends around the midpost 108a of the extension limiting stop 49 and around the pivotal connector 64, 89 to bias the extension limiting stop 49 radially inward in a direction substantially perpendicular to the axis of rotation of the hinge 314 toward the pivotal connector 64, 89 and away from the forward arcs 44a, 44b of the peripheral edges 42a, 42b.

Three embodiments of means for biasing the extension and flexion limiting stops 49, 53 radially inward in a direction substantially perpendicular to the axis of hinge rotation toward the pivotal connector 64, 89 and away from the peripheral edges 42a, 42b have been described herein. It is apparent to the skilled artisan, however, that other means are available in accordance with the present teaching for biasing the extension and flexion limiting stops radially inward in a direction substantially perpendicular to the axis of hinge rotation and that such means fall within the scope of the present invention. It is further noted that the pivotal connector 64, 89 has been disclosed herein as providing means about which the hinge 14, 214 or 314 rotates and additionally acting as a biasing anchors providing means for anchoring the biasing assemblies 90, 290 or 390. It is apparent to the skilled artisan, however, that other means (i.e., biasing anchors) are available in accordance with the teaching herein for anchoring the biasing assemblies independent of the pivotal connector 64, 89 wherein such biasing anchors are positioned radially inward from the peripheral edges 42a, 42b, and wherein the biasing assemblies 90, 290, or 390 engage such biasing anchors, thereby connecting the stops 49, 53 to the biasing anchors and biasing the stops 49, 53 radially inward from the peripheral edges 42a, 42b. It is further apparent to the skilled artisan that such biasing anchors means fall within the scope of the present invention.

METHOD OF OPERATION

Figure 6A:
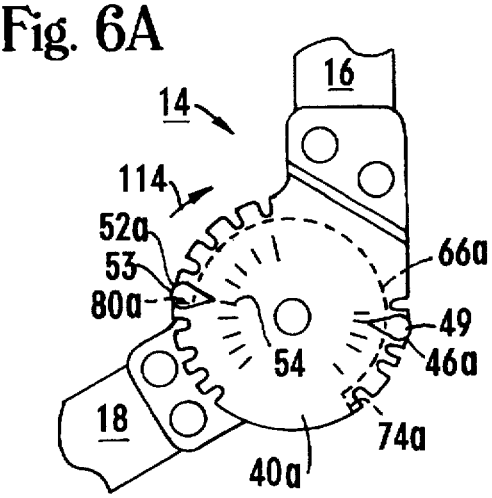
FIG. 6A is a frontal view of the hinge of FIG. 1 in a rotational mode of operation, wherein the hinge is rotated in a first direction to a preselected flexion limit.

The modes of hinge operation are described hereafter with reference to FIGS. 6A, 6B, 6C, 6D and 7. Hinge operation is described for purposes of illustration with reference to the hinge 14, but it is understood that this description applies generally to all hinges of the present invention having alternate biasing means including the hinges 214 and 314. Referring initially to FIG. 6A, the hinge 14 is shown in the rotational mode of operation, wherein the lower arm 18 of the brace is rotated about the hinge 14 in a first clockwise direction of rotation indicated by the arrow 114 until the hinge 14 reaches a flexion limit of 60° that has been preselected from a number of flexion limits including 10°, 20°, 30°, 45°, 60°, 75°, 90°, 105°, and 120°. The flexion limit is preselected by positioning the flexion limiting stop 53 in the flexion limiting notch 52a of the anterior outer member 40a corresponding to 60° as indicated by the rotation limit marker 54 adjacent to the flexion limiting notch 52a. The flexion limiting stop 53 is retained in the flexion limiting notch 52a by the biasing assembly, as described above and shown in FIG. 3. At the flexion limit, the flexion limiting face 80a of the anterior inner member 66a shown in phantom beneath the anterior outer member 40a abuts the flexion limiting stop 53 preventing further rotation of the hinge 14 in the direction of the arrow 114, thereby limiting flexion of the knee joint. Although not shown in FIG. 6A, it is apparent that, at the preselected flexion limit, the flexion limiting stop 53 is simultaneously positioned in the corresponding flexion limiting notch 52b of the posterior outer member 40b and the flexion limiting face 80b of the posterior inner member 66b abuts the flexion limiting stop 53.

Figure 6B:
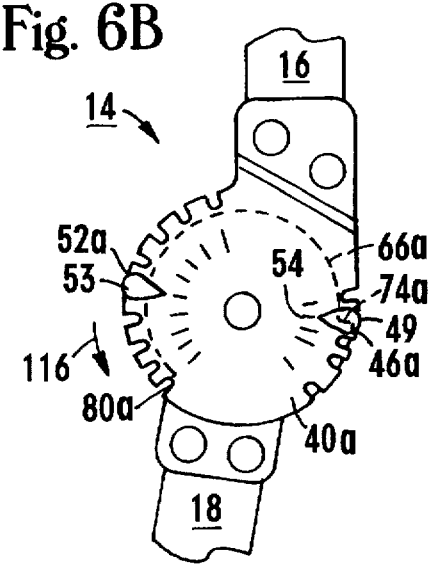
FIG. 6B is a frontal view of the hinge of FIG. 1 in a rotational mode of operation, wherein the hinge is rotated in a second direction to a preselected extension limit.

Referring to FIG. 6B, the hinge 14 is shown in the rotational mode of operation, wherein the lower arm 18 of the brace is rotated about the hinge 14 in a second counterclockwise direction of rotation indicated by the arrow 116 until the hinge 14 reaches an extension limit of 10° that has been preselected from a number of extension limits including 0°, 10°, 20°, and 30°. In a manner similar to that described above with respect to the flexion limit, the extension limit is preselected by positioning the extension limiting stop 49 in the extension limiting notch 46a of the anterior outer member 40a corresponding to 10° as indicated by the rotation limit mark 54 adjacent to the extension limiting notch 46a. The extension limiting stop 49 is retained in the extension limiting notch 46a by the biasing assembly, as described above and shown in FIG. 3. At the extension limit, the extension limiting face 74a of the anterior inner member 66a abuts the extension limiting stop 49 preventing further rotation of the hinge 14 in the direction of the arrow 116, thereby limiting extension of the knee joint. Although not shown in FIG. 6B, it is apparent that, at the preselected extension limit, the extension limiting stop 49 is also positioned in the corresponding extension limiting notch 46b of the posterior outer member 40b and the extension limiting face 74b of the posterior inner member 66b abuts the extension limiting stop 49.

Figure 6C:
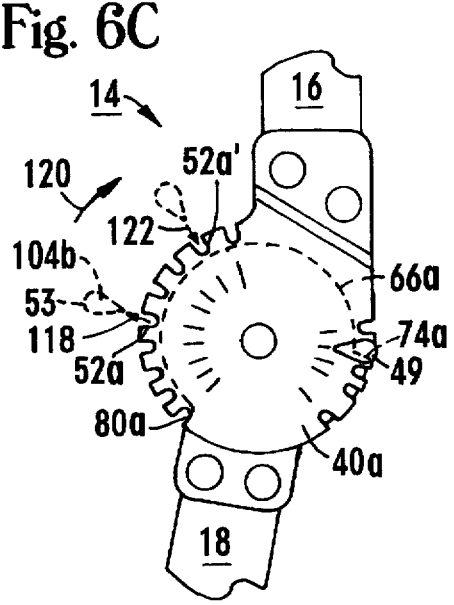
FIG. 6C is a frontal view of the hinge of FIG. 1 in an adjustment mode of operation, wherein the flexion limit of the hinge is adjusted from that of FIG. 6A.

Referring to FIG. 6C, the hinge 14 is shown in the adjustment mode of operation, wherein the flexion limit is adjusted by repositioning the flexion limiting stop 53 from the flexion limiting notch 52a of the anterior outer member 40a corresponding to 60° to the flexion limiting notch 52a' corresponding to 105°. The flexion limiting stop 53 is repositioned by manually grasping the anterior and posterior heads 104b, 110b of the flexion limiting stop 53 and drawing the flexion limiting stop 53 radially outward away from the anterior outer member 40a in the direction of the arrow 118 counter to the radially inward biasing force of the biasing assembly (not shown). When the flexion limiting stop 53, shown in phantom, clears the flexion limiting notch 52a, the flexion limiting stop 53 is circumferentially rotated in association with the biasing assembly along the peripheral edge 42a of the anterior outer member 40a in the direction of the arrow 120. The anterior head 104b of the flexion limiting stop 53 is released when the flexion limiting stop 53 is radially adjacent to the flexion limiting notch 52a'. The biasing assembly urges the flexion limiting stop 53 radially inward in the direction of the arrow 122 until it is received by the flexion limiting notch 52a'. Although not shown in FIG. 6C, it is apparent that, at the adjusted flexion limit, the flexion limiting stop 53 is simultaneously positioned in the corresponding flexion limiting notch 52b' of the posterior outer member 40b. Adjustment of the extension limit can also be performed in the present adjustment mode of operation in a like manner readily apparent to the skilled artisan. Upon completion of the adjustment mode of operation, rotational operation of the hinge 14 is resumed with the hinge 14 having an adjusted flexion or extension limit.

Figure 6D:
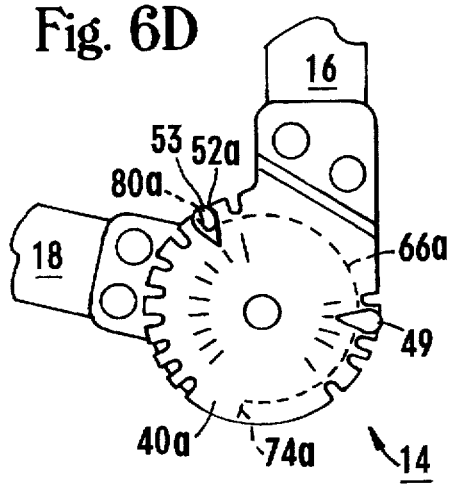
FIG. 6D is a frontal view of the hinge of FIG. 1 in a rotational mode of operation, wherein the hinge is rotated in the first direction to the adjusted flexion limit of FIG. 6C.

Referring to FIG. 6D, the hinge 14 is shown in the rotational mode of operation, wherein the lower arm 18 of the brace is rotated about the hinge 14 until the hinge 14 reaches the adjusted flexion limit selected in accordance FIG. 6C. Operation of the hinge 14 with the adjusted flexion limit is substantially the same as described above with respect to FIG. 6A.

Figure 7:
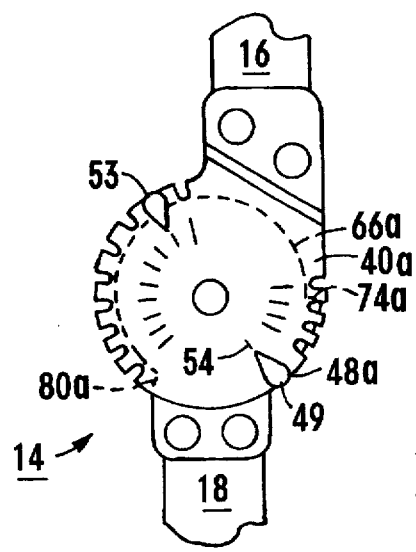
FIG. 7 is frontal view of the hinge of FIG. 1 in a locked mode of operation, wherein the hinge is locked against rotation.

Referring to FIG. 7, the hinge 14 is shown in the locked mode of operation, wherein the hinge 14 is locked at an extension angle of 0° against rotation in either direction. The locked mode is achieved by positioning the extension limiting stop 49 in the locking notch 48a of the anterior outer member 40a as indicated by the rotation limit marker 54 adjacent thereto. The extension limiting stop 49 is retained in the locking notch 48a by the biasing assembly, as described above and shown in FIG. 3. With the extension limiting stop 49 positioned in this manner, rotation of the hinge 14 in either direction is blocked. Although not shown in FIG. 7, it is apparent that, in the locked mode of operation, the extension limiting stop 49 is also simultaneously positioned in the corresponding locking notches 46b, 76a, 76b of the posterior outer member 40b, the anterior inner member 66a, and the posterior inner member 66b, respectively. It is further apparent to the skilled artisan that the hinge 14 can be modified by relocating the locking notches 48a, 48b, 76a, 76b to other locations on the forward arcs 44a, 72a or to locations on the rearward arcs 50a, 78a, enabling a locked mode of hinge operation at other fixed angles of flexion or extension.

While the particular hinge for an orthopedic brace having an adjustable range of rotation as herein shown and disclosed in detail is fully capable of obtaining the objects and providing the advantages hereinbefore stated, it is to be understood that the hinge is merely illustrative of presently preferred embodiments of the invention and that other embodiments are possible within the scope of the present invention.

We claim:

1. A hinge for an orthopedic brace comprising:

a first member having a first peripheral edge;

a second member having a second peripheral edge;

a pivotal connector connecting said first and second members;

a notch formed in said first peripheral edge;

a limiting face formed in said second member;

a stop selectively positionable in said notch and engageable with said limiting face upon rotation of said second member relative to said first member;

a biasing assembly biasing said stop radially inward from said first peripheral edge; and a biasing anchor positioned radially inward from said first peripheral edge, wherein said biasing assembly engages said stop and said biasing anchor, thereby connecting said stop to said biasing anchor and biasing said stop radially inward from said peripheral edge, and further wherein said biasing assembly comprises a slidable member engaging said stop and a spring elastically engaging said slidable member and said biasing anchor such that said stop is rotatable and elastically radially displacable relative to said first member.

2. A hinge as recited in claim 1, wherein said biasing anchor is said pivotal connector.

3. A hinge for an orthopedic brace comprising:

a first member having a first peripheral edge;

a second member having a second peripheral edge;

a pivotal connector connecting said first and second members;

a notch formed in said first peripheral edge;

a limiting face formed in said second member;

a stop selectively positionable in said notch and engageable with said limiting face upon rotation of said second member relative to said first member;

a biasing assembly biasing said stop radially inward from said first peripheral edge; and a biasing anchor positioned radially inward from said first peripheral edge, wherein said biasing assembly engages said stop and said biasing anchor, thereby connecting said stop to said biasing anchor and biasing said stop radially inward from said peripheral edge, and further wherein said biasing assembly comprises an elastic band elastically engaging said stop and said biasing anchor.

4. A hinge for an orthopedic brace comprising:

a first member having a first peripheral edge;

a second member having a second peripheral edge;

a pivotal connector connecting said first and second members;

a first notch formed in said first peripheral edge; a second notch formed in said first peripheral edge at a spaced interval from said first notch;

a limiting face formed in said second member;

a stop selectively positionable in said first notch and engageable with said limiting face, thereby defining a first range of rotation of said hinge, and said stop selectively positionable in said second notch and engageable with said limiting face, thereby defining a second range of rotation of said hinge; and a biasing assembly biasing said stop radially inward from said first peripheral edge.

5. A hinge as recited in claim 4, wherein said stop is an extension limiting stop, said limiting face is an extension limiting face, and said first and second notches are a set of extension limiting notches formed in a first side of said first peripheral edge, and said hinge further comprises a flexion limiting face formed in said second peripheral edge and a set of flexion limiting notches including a first flexion limiting notch and a second flexion limiting notch formed in a second side of said first peripheral edge opposite said first side.

6. A hinge as recited in claim 5, wherein said extension limiting stop positioned in said first extension limiting notch defines an extension limit of said first range of rotation and said extension limiting stop positioned in said second extension limiting notch defines an extension limit of said second range of rotation, and said hinge further comprises a flexion limiting stop selectively positionable in said first or said second flexion limiting notch and engageable with said flexion limiting face upon rotation of said second member relative to said first member, wherein said flexion limiting stop positioned in said first flexion limiting notch defines a flexion limit of said first range of rotation and said flexion limiting stop positioned in said second flexion limiting notch defines a flexion limit of said second range of rotation.

7. A hinge for an orthopedic brace comprising:

a first member having a first peripheral edge;

a second member having a second peripheral edge;

a pivotal connector connecting said first and second members;

a notch formed in said first peripheral edge;

a limiting face formed in said second member;

a stop selectively positionable in said notch and engageable with said limiting face upon rotation of said second member relative to said first member;

a biasing assembly biasing said stop radially inward from said first peripheral edge; and a locking notch formed in said second peripheral edge wherein said stop is selectively positionable in said locking notch and in said notch formed in said first peripheral edge, thereby locking said second member against rotation relative to said first member.

8. A hinge for an orthopedic brace comprising:

a first member having a first peripheral edge;

a second member having a second peripheral edge;

a pivotal connector connecting said first and second members;

a notch formed in said first peripheral edge;

a limiting face formed in said second member;

a stop selectively positionable in said notch and engageable with said limiting face upon rotation of said second member relative to said first member;

a biasing assembly biasing said stop radially inward from said first peripheral edge; and a rotation limit marker aligned with said notch wherein said stop has a pointer alignable with said rotation limit marker when said stop is positioned in said notch.

9. A hinge for an orthopedic brace comprising:

an outer anterior member having a first peripheral edge;

an inner anterior member having a second peripheral edge;

a pivotal connector connecting said outer and inner anterior members;

an anterior notch formed in said first peripheral edge;

an anterior limiting face formed in said inner anterior member;

a stop selectively positionable in said anterior notch and engageable with said anterior limiting face upon rotation of said inner anterior member relative to said outer anterior member;

a biasing assembly biasing said stop radially inward from said first peripheral edge;

an outer posterior member having a posterior notch formed therein aligned with said anterior notch; and an inner posterior member having a limiting face aligned with said anterior limiting face, wherein said anterior and posterior outer and inner members are parallelly aligned and rotatably connected by said pivotal connector.

10. A hinge for an orthopedic brace comprising:

a first member having a first peripheral edge;

a second member having a second peripheral edge;

a pivotal connector connecting said first and second members;

a rotation limiting notch formed in said first peripheral edge;

a limiting face formed in said second member;

a stop selectively positionable in said rotation limiting notch and engageable with said limiting face upon rotation of said second member relative to said first member;

a biasing assembly biasing said stop radially inward from said first peripheral edge;

an outer locking notch formed in said first peripheral edge at a spaced interval from said rotation limiting notch; and an inner locking notch formed in said second peripheral edge, wherein said stop is selectively positionable in said outer and inner locking notches, thereby locking said second member from rotation relative to said first member.

11. A hinge for an orthopedic brace comprising:
a first member having a first peripheral edge;
a second member having a second peripheral edge;
a pivotal connector connecting said first and second members;
a notch formed in said first peripheral edge;
a limiting face formed in said second member;
a stop selectively positionable in said notch and engageable with said limiting face upon rotation of said second member relative to said first member;
means for biasing said stop radially inward from said first peripheral edge; and
a biasing anchor positioned radially inward from said first peripheral edge, wherein said biasing means engages said stop and said biasing anchor, thereby connecting said stop to said biasing anchor and biasing said stop radially inward from said peripheral edge, and further wherein said biasing means comprises a slidable member engaging said stop and a spring elastically engaging said slidable member and said biasing anchor such that said stop is rotatable and elastically radially displacable relative to said first member.

12. A hinge as recited in claim 11, wherein said biasing anchor is said pivotal connector.

13. A hinge for an orthopedic brace comprising:
a first member having a first peripheral edge;
a second member having a second peripheral edge;
a pivotal connector connecting said first and second members;
a notch formed in said first peripheral edge;
a limiting face formed in said second member;
a stop selectively positionable in said notch and engageable with said limiting face upon rotation of said second member relative to said first member;
means for biasing said stop radially inward from said first peripheral edge; and
a biasing anchor positioned radially inward from said first peripheral edge, wherein said biasing means engages said stop and said biasing anchor, thereby connecting said stop to said biasing anchor and biasing said stop radially inward from said peripheral edge, and further wherein said biasing means comprises an elastic band elastically engaging said stop and said biasing anchor.

14. A hinge for an orthopedic brace comprising:
a first member having a first peripheral edge;
a second member having a second peripheral edge;
a pivotal connector connecting said first and second members;
a first notch formed in said first peripheral edge; a second notch formed in said first peripheral edge at a spaced interval from said first notch;
a limiting face formed in said second member;
a stop selectively positionable in said first notch and engageable with said limiting face, thereby defining a first range of rotation of said hinge, and said stop selectively positionable in said second notch and engageable with said limiting face, thereby defining a second range of rotation of said hinge; and
means for biasing said stop radially inward from said first peripheral edge.

15. A hinge as recited in claim 14, wherein said stop is an extension limiting stop, said limiting face is an extension limiting face, and said first and second notches are a set of extension limiting notches formed in a first side of said first peripheral edge, and said hinge further comprises a flexion limiting face formed in said second peripheral edge and a set of flexion limiting notches including a first flexion limiting notch and a second flexion limiting notch formed in a second side of said first peripheral edge opposite said first side.

16. A hinge as recited in claim 15, wherein said extension limiting stop positioned in said first extension limiting notch defines an extension limit of said first range of rotation and said extension limiting stop positioned in said second extension limiting notch defines an extension limit of said second range of rotation, and said hinge further comprises a flexion limiting stop selectively positionable in said first or said second flexion limiting notch and engageable with said flexion limiting face upon rotation of said second member relative to said first member, wherein said flexion limiting stop positioned in said first flexion limiting notch defines a flexion limit of said first range of rotation and said flexion limiting stop positioned in said second flexion limiting notch defines a flexion limit of said second range of rotation.

17. A hinge for an orthopedic brace comprising:
an outer anterior member having a first peripheral edge;
an inner anterior member having a second peripheral edge;
a pivotal connector connecting said outer and inner anterior members;
an anterior notch formed in said first peripheral edge;
an anterior limiting face formed in said inner anterior member;
a stop selectively positionable in said anterior notch and engageable with said anterior limiting face upon rotation of said inner anterior member relative to said outer anterior member;
means for biasing said stop radially inward from said first peripheral edge;
an outer posterior member having a posterior notch formed therein aligned with said anterior notch; and
an inner posterior member having a limiting face aligned with said anterior limiting face, wherein said anterior and posterior outer and inner members are parallelly aligned and rotatably connected by said pivotal connector.

18. A hinge for an orthopedic brace comprising:
a first member having a first peripheral edge;
a second member having a second peripheral edge;
a pivotal connector connecting said first and second members;
a first notch and a second notch formed in said first peripheral edge at a spaced apart interval;
a limiting face formed in said second member;
a stop selectively positionable in said first notch and engageable with said limiting face, thereby defining a first range of rotation of said hinge, and said stop selectively positionable in said second notch and engageable with said limiting face, thereby defining a second range of rotation of said hinge;
means for biasing said stop radially inward from said first peripheral edge; and
a biasing anchor positioned radially inward from said first peripheral edge, wherein said biasing means engages said stop and said biasing anchor, thereby connecting said stop to said biasing anchor and biasing said stop radially inward from said peripheral edge, and further wherein said biasing means comprises a slidable member engaging said stop and a spring elastically engaging said slidable member and said biasing anchor such that said stop is rotatable and elastically radially displacable relative to said first member.

19. A hinge as recited in claim 18, wherein said biasing means comprises an elastic band elastically engaging said stop and said biasing anchor.

20. A hinge for an orthopedic brace comprising:

a first member having a first peripheral edge;

a second member having a second peripheral edge;

a pivotal connector connecting said first and second members;

a set of extension limiting notches including a first extension limiting notch and a second extension limiting notch formed in a first side of said first peripheral edge at a spaced apart interval;

an extension limiting face formed in said second member;

an extension limiting stop selectively positionable in said first extension limiting notch and engageable with said extension limiting face, thereby defining a first range of rotation of said hinge, and said stop selectively positionable in said second notch and engageable with said extension limiting face, thereby defining a second range of rotation of said hinge;

means for biasing said stop radially inward from said first peripheral edge; and a flexion limiting face formed in said second peripheral edge; and a set of flexion limiting notches including a first flexion limiting notch and a second flexion limiting notch formed in a second side of said first peripheral edge opposite said first side.

21. A hinge as recited in claim 20, wherein said extension limiting stop positioned in said first extension limiting notch defines an extension limit of said first range of rotation and said extension limiting stop positioned in said second extension limiting notch defines an extension limit of said second range of rotation, and said hinge further comprises a flexion limiting stop selectively positionable in said first or said second flexion limiting notch and engageable with said flexion limiting face upon rotation of said second member relative to said first member, wherein said flexion limiting stop positioned in said first flexion limiting notch defines a flexion limit of said first range of rotation and said flexion limiting stop positioned in said second flexion limiting notch defines a flexion limit of said second range of rotation.

22. A hinge for an orthopedic brace comprising:

an outer anterior member having a first peripheral edge;

an inner anterior member having a second peripheral edge;

a pivotal connector connecting said outer and inner anterior members;

an anterior notch and a second notch formed in said first peripheral edge at a spaced apart interval;

an anterior limiting face formed in said inner anterior member;

a stop selectively positionable in anterior notch and engageable with said limiting face, thereby defining a first range of rotation of said hinge, and said stop selectively positionable in said second notch and engageable with said limiting face, thereby defining a second range of rotation of said hinge;

means for biasing said stop radially inward from said first peripheral edge; an outer posterior member having a posterior notch formed therein aligned with said anterior notch; and an inner posterior member having a limiting face aligned with said anterior limiting face, wherein said anterior and posterior outer and inner members are parallelly aligned and rotatably connected by said pivotal connector.

* * * * *